United States Patent
Luo et al.

(10) Patent No.: US 8,066,102 B2
(45) Date of Patent: Nov. 29, 2011

(54) LIFTING APPARATUS AND SAFETY INSPECTION SYSTEM

(75) Inventors: Xilei Luo, Beijing (CN); Kejun Kang, Beijing (CN); Yinong Liu, Beijing (CN); Yuanjing Li, Beijing (CN); Zhiqiang Chen, Beijing (CN); Wanlong Wu, Beijing (CN); Yulan Li, Beijing (CN); Li Zhang, Beijing (CN); Ziran Zhao, Beijing (CN); Bin Sang, Beijing (CN); Hailin Wang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 1028 days.

(21) Appl. No.: 11/525,697

(22) Filed: Sep. 22, 2006

(65) Prior Publication Data

US 2007/0062253 A1 Mar. 22, 2007

(30) Foreign Application Priority Data

Sep. 22, 2005 (CN) .......................... 2005 1 0086460

(51) Int. Cl.
  *B66B 9/02* (2006.01)
  *H01L 21/68* (2006.01)
  *G21K 5/10* (2006.01)
(52) U.S. Cl. .......... 187/267; 414/672; 414/757; 378/69; 378/180
(58) Field of Classification Search ................. 187/214, 187/267; 254/98, 7 R; 248/131, 656, 669; 702/40, 81; 211/103, 163, 166, 207; 414/672, 414/757; 378/57, 69, 180, 208
See application file for complete search history.

(56) References Cited

U.S. PATENT DOCUMENTS

| | | | | |
|---|---|---|---|---|
| 3,309,060 A * | 3/1967 | Villars | ........................ | 254/7 C |
| 4,251,730 A * | 2/1981 | Cushman et al. | ............... | 378/40 |
| 4,281,744 A * | 8/1981 | Koerber | ........................ | 414/663 |
| 4,919,236 A * | 4/1990 | Karlsson et al. | ............... | 187/268 |
| 4,989,225 A * | 1/1991 | Gupta et al. | ..................... | 378/10 |
| 5,125,791 A * | 6/1992 | Volovich | ........................ | 348/446 |
| 5,156,166 A * | 10/1992 | Sebring | ........................ | 5/608 |
| 5,317,617 A * | 5/1994 | Lange | ............................ | 378/65 |
| 5,546,179 A * | 8/1996 | Cheng | ............................ | 356/73 |
| 5,951,776 A * | 9/1999 | Selyutin et al. | ............... | 118/729 |
| 2002/0127089 A1* | 9/2002 | Stone et al. | ................... | 414/672 |

FOREIGN PATENT DOCUMENTS

| | | |
|---|---|---|
| CN | 2183848 Y | 11/1994 |
| CN | 2255973 Y | 6/1997 |
| CN | 2368821 Y | 3/2000 |

(Continued)

OTHER PUBLICATIONS

Chinese First Office Action in foreign counterpart Application No. 200510086460.1, dated May 22, 2009.

(Continued)

*Primary Examiner* — Michael Mansen
*Assistant Examiner* — Stefan Kruer
(74) *Attorney, Agent, or Firm* — Kinney & Lange, P.A.

(57) ABSTRACT

A lifting apparatus includes a vertical guide device, a turntable device which is movable along the vertical guide device upwards or downwards, and a first driving device which drives the turntable device moving in an upward and downward direction guided by the vertical guide device. The turntable device includes a bracket which is slidably engaged with the vertical guide device and projects perpendicularly toward a side of the vertical guide device, a turntable which is rotatably provided on the bracket, and a second driving device which rotates the turntable on the bracket.

9 Claims, 4 Drawing Sheets

FOREIGN PATENT DOCUMENTS

| | | |
|---|---|---|
| JP | 6064235 A | 3/1994 |
| WO | WO 9414695 A1 * | 7/1994 |

OTHER PUBLICATIONS

Chinese Second Office Action in foreign counterpart Application No. 200510086460.1, dated Oct. 16, 2009.

Chinese Third Office Action in foreign counterpart Application No. 200510086460.1, dated Mar. 10, 2010.

Summary of Chinese Office Actions (NPL Cites 1, 2, and 3) and related prosecution of foreign counterpart Application No. 200510086460.1 in English.

* cited by examiner

LIFTING APPARATUS AND SAFETY INSPECTION SYSTEM

FIELD OF THE INVENTION

The present invention relates to a lifting apparatus with a turntable and safety inspection system with the same, which is adapted to a kind of CT safety inspection apparatus for liquid articles using radiation

BACKGROUND OF THE INVENTION

A turntable and lifting mechanisms popularly used in publicly known industrial CT normally comprising of two independent systems. Objects to be detected can be rotated on the turntable mechanism without lifting movement. An X-ray generator and a detector are respectively mounted on two lifting mechanisms with only lifting movement. Thus, there are some disadvantages for an apparatus manufactured by a technical solution utilizing this form of kinematic pair, such as complicated structures, bulky volume and high cost.

SUMMARY OF THE INVENTION

The present invention has been made to overcome the above mentioned disadvantages existing in prior art and to achieve the function of inspecting liquid article. Accordingly, the object of the present invention is to provide a lifting apparatus, which combines a rotating mechanism and a lifting mechanism as a single apparatus, thus realizing the self rotation and elevation of the objects to be detected, and a safety inspection system thereof.

To achieve the above-mentioned object, the technical solution of the present invention is provided as following:

A lifting apparatus with a turntable, comprising a vertical guide device; a turntable device which is movable along the vertical guide device in the upward or downward direction; and a first driving device which drives the turntable device moving in an upward or downward direction guided by the vertical guide device. Wherein said turntable device comprises a bracket which is slidably engaged with the vertical guide device and projects perpendicularly toward a side of the vertical guide device; a turntable which is rotatably provided on the bracket; and a second driving device which can rotate the turntable on the bracket.

According to the lift apparatus, the vertical guide device comprises a linear slide rail which is embedded in by the outer edge of the bracket to form linear constraint therebetween; a lead screw which is provided in the linear slide rail, with the first driving device provided at an end of the linear slide rail to drive the lead screw to rotate; and a nut which is fixed on the bracket and engaged with the lead screw.

According to the lift apparatus, an upper bearing seat and a lower bearing seat are provided at two ends of the linear slide rail respectively, the lead screw is engaged with the upper bearing seat and lower bearing seat via a sliding bearing.

According to the lift apparatus, the sliding bearing comprises a second radial bearing and a second thrust bearing.

According to the lift apparatus, the outer edge of the bracket is movably embedded with the linear slide rail in a manner that V-shape bosses are provided on the bracket and V-shape grooves mated with the V-shape boss are provided in the linear slide rail.

According to the lift apparatus, the outer edge of the bracket is movably embedded with the linear slide rail in a manner that a ball bearing type linear slide rail is provided on the linear slide rail and the outer edge of the slider bracket is provided with an embedding block connected with the ball bearing type linear slide rail.

According to the lift apparatus, proximity switches for limiting position and protecting function are provided at the top and bottom of the linear slide rail.

According to the lift apparatus, a first radial bearing and a first thrust bearing are arranged between the turntable and the bracket.

According to the lift apparatus, a flexible coupling is provided between an end of the lead screw and the first driving device.

According to the lift apparatus, a counterbore for centrally positioning a standard sample is provided at the central place of the turntable, and a rubber pad is provided on the turntable.

According to the lift apparatus, a power transmission opening of the second driving device is provided with a cable chain projecting from the guide device.

According to the lift apparatus, a safety inspection system, comprising any one of above-mentioned lifting apparatuses; and a CT device provided above the turntable device.

In light of the technical solutions disclosed in the present invention, the following beneficial advantages can be obtained:

1. Articles can be spirally scanned in the manner disclosed in the present invention.
2. Data acquisition can be correctly ensured, since the movement precision is enhanced by the adoption of ball screw.
3. The friction resistance can be reduced, the transmission efficiency can be improved and the noise can be decreased by the adoption of the ball screw.

BRIEF DESCRIPTION OF THE DRAWINGS

The above and other objects, and features, and advantages of certain embodiments of the invention will be more apparent from the following description taken in conjunction with the accompanying drawings, in which.

DETAILED DESCRIPTION OF THE PREFERRED EMBODIMENT

Figure 1:
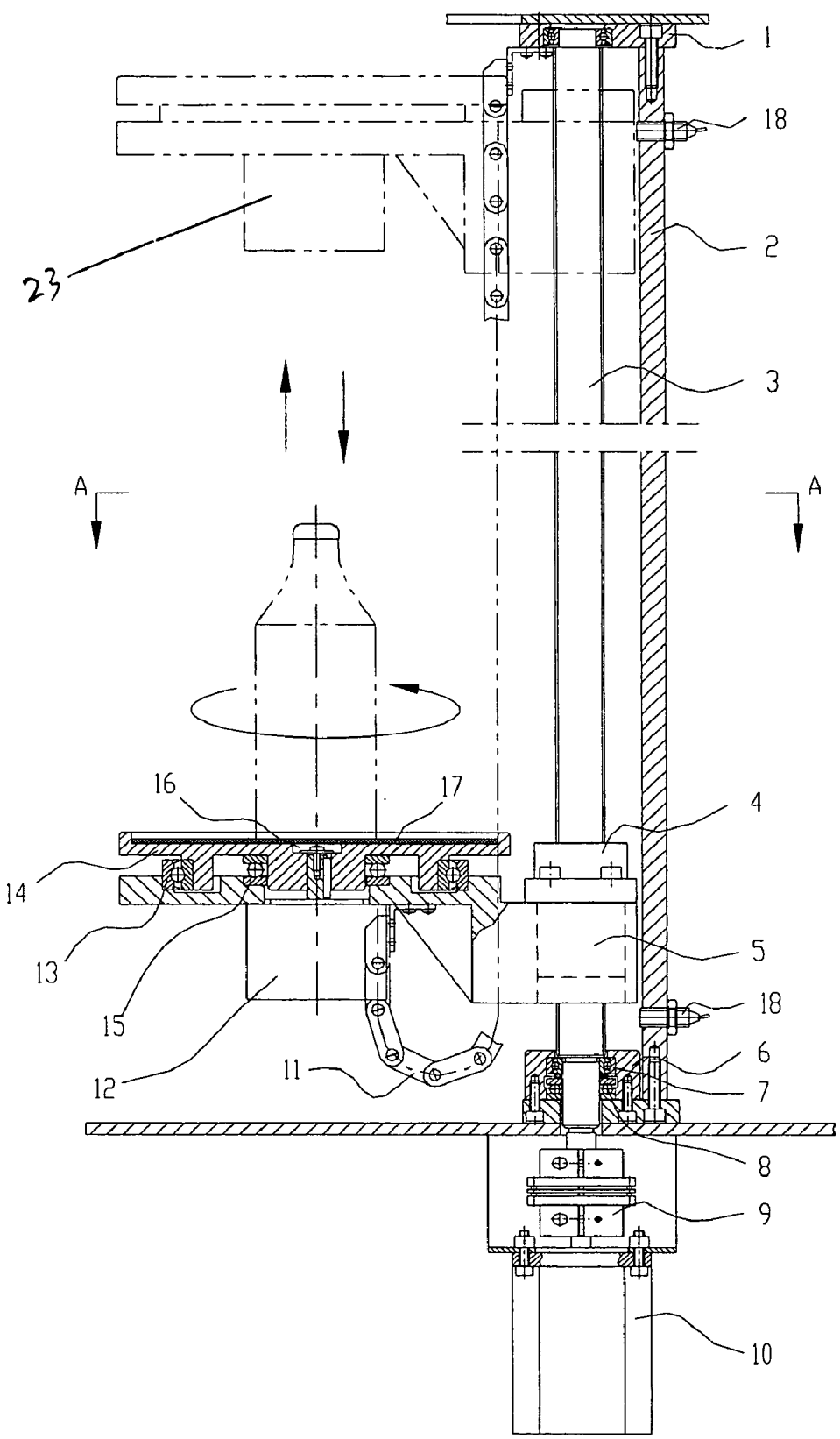
FIG. 1 is a general structural view of the lifting apparatus with a turntable according to first embodiment of the present invention.

Reference will now be made in detail to the present preferred embodiments of the present invention, examples of which are illustrated in the accompanying drawings, wherein like reference numerals refer to like elements throughout. The embodiments are described below in order to explain the present invention by referring to the figures.

Figure 2:
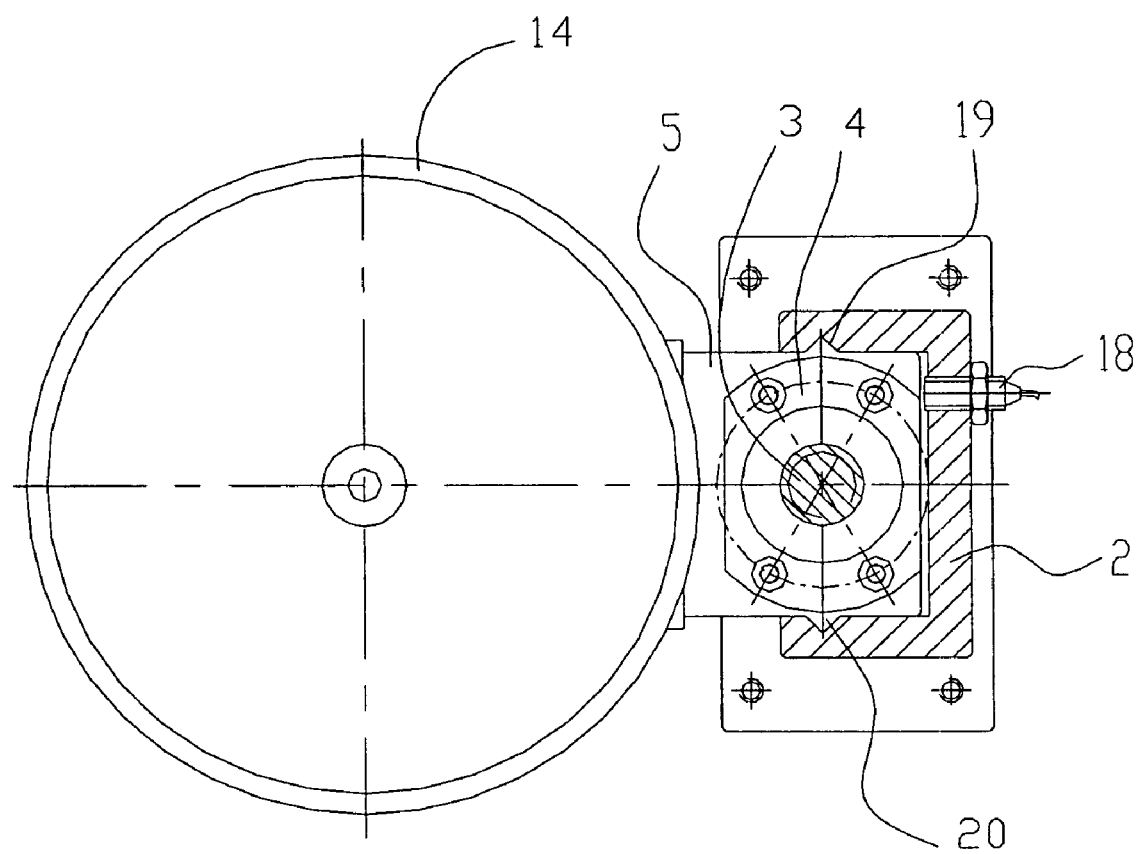
FIG. 2 is a sectional view of FIG. 1 along line A-A.

FIG. 1 and FIG. 2 show the general structure of the lifting apparatus and safety inspection system according to the first embodiment of the present invention. The lifting apparatus comprises a vertical guide device, a turntable device which is movable along the vertical guide device in the upward and downward direction, and a first driving device, such as a first motor 10, which drives the turntable device moving upwards or downwards along the direction guided by the vertical guide device. The turntable device comprises a slider type bracket 5 which is slidably engaged with the vertical guide device and projects vertically toward a side of the vertical guide device, a turntable 14 which rotatably provides on the bracket 5, and a second driving device, such as a second motor 12, which rotates the turntable 14 on the bracket 5.

The vertical guide device comprises: a linear slide rail 2 which is movably embedded with the outer edge of the bracket 5 to form linear constraint between them so that the bracket 5 is not rotatable with respect to the linear slide rail 2; a lead screw 3 that provided in the linear slide rail 2, with the first motor 10 provided at an end of the linear slide rail 2, preferably on the bottom of the linear slide rail 2, to rotate the lead screw 3; and a nut 4 that is fixed on the bracket 5 and is engaged with the lead screw 3.

An upper bearing seat 1 and a lower bearing seat 6 are provided at two ends of the linear slide rail 2 respectively. The lower bearing seat 6 is provided with a second radial bearing 7 for positioning and a second thrust bearing 8 for bearing a load applied on the lead screw 3 in the vertical direction. The top and bottom of the linear slide rail 2 are both provided with limit switches 18 for position restriction purpose, the limit switches can control the lifting START/STOP positions of the turntable 14. The lead screw 3 provided in the linear slide rail 2 is engaged with the upper bearing seat 1 and lower bearing seat 6 by a sliding bearing comprised of the second radial bearing 7 and the second thrust bearing 8. The nut 4 can reciprocate on the lead screw 3, and the bottom end of the lead screw 3 is connected with the first motor 10 by a flexible coupling 9.

The slider bracket 5 is threadedly connected with the nut 4. The second motor 12 is provided on the bottom surface of the slider bracket 5. The turntable 14 is provided on the upper part of the slider bracket 5. A first radial bearing 13 and a thrust bearing 15 are arranged between the turntable 14 and the slider bracket 5, which are used for positioning and load bearing. A counterbore 16 for centrally positioning a standard sample is provided at the central place of the turntable 14, so that the standard sample database can be precisely obtained. A rubber pad 17 is provided on the turntable 14 to prevent the objects to be detected from moving which may negatively influence the precision of the image acquisition during rotation. The rotation of the turntable 14 is realized by the second motor 12. A cable wire is provided in the cable chain 11 for protection so that intertwisting of the cable wire in the second motor 12 during rotation can be prevented.

V-shape grooves 19 are provided on the two side walls of the linear slide rail 2. And V-shape bosses 20 mating with the V-shape grooves 19 are provided on the slider bracket 5 and are slidably engaged with the V-shape groove 19 on the two side walls of the linear slide rail 2, so that the rotation of the slider bracket 5 round the linear slide rail 2 can be prevented and the slider bracket 5 can move along the V-shape grooves 19 of the two side walls of the slider bracket 5. Thus, the outer edge of the bracket 5 can movably embedded with the linear slide rail for linear constraint.

Alternatively, the engaging manner of the lead screw 3 with nut 4 in the vertical guide device can be replaced with a belt or sling structure. For example, an end of the belt or sling is fixed on the reel device driven by the first motor 10, with the other end thereof fixed on the turntable apparatus. Further, the belt or sling is intermediately transmitted by related pulley structures. Thus, the lifting of the turntable device is achieved with the rotation of the first motor 10. Further alternatively, the engaging manner of the lead screw 3 with nut 4 in the vertical guide device can be replaced with a structure in which a gear is engaged with a rack.

Figure 3:
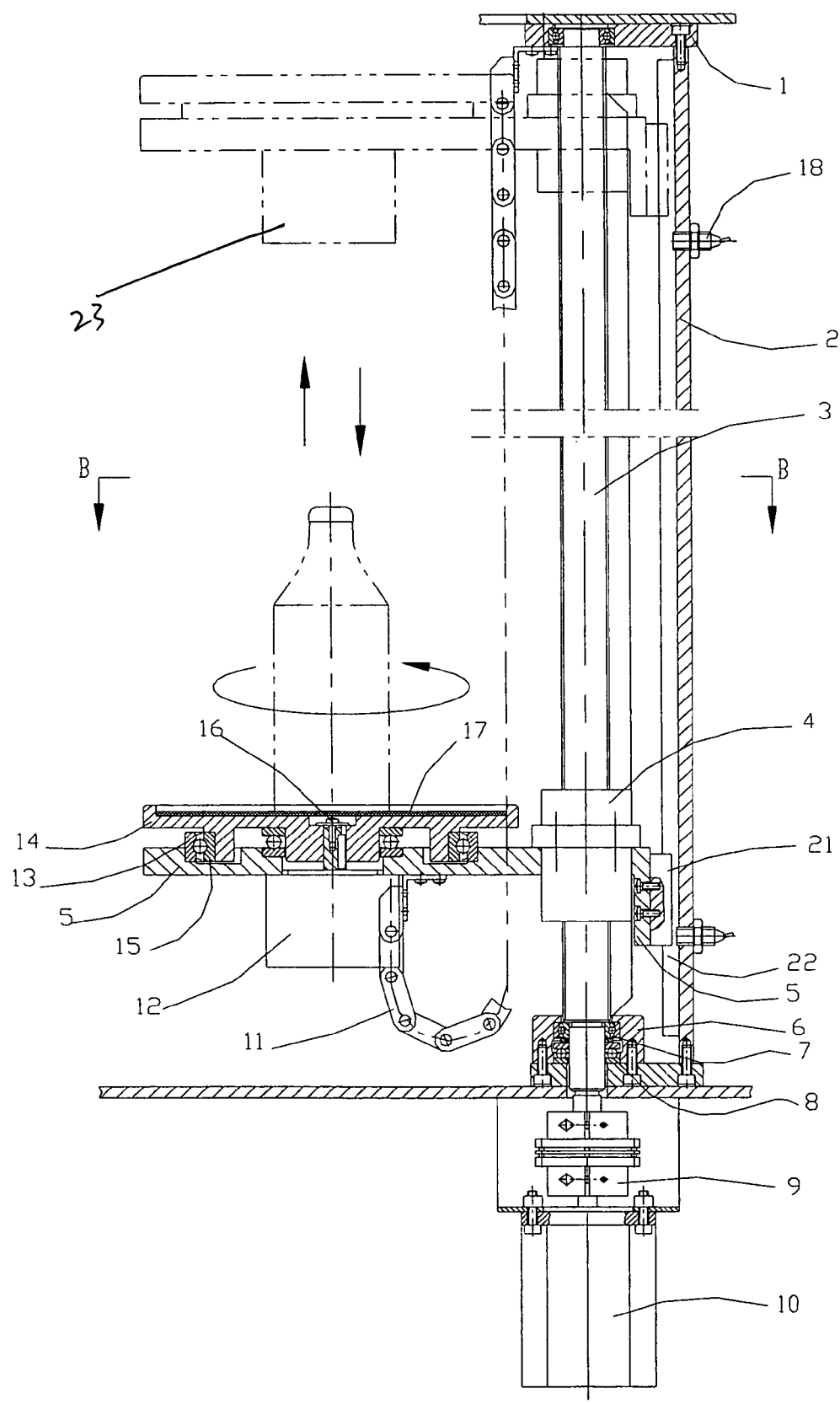
FIG. 3 is a general structural view of the lifting apparatus with a turntable according to second embodiment of the present invention.
Figure 4:
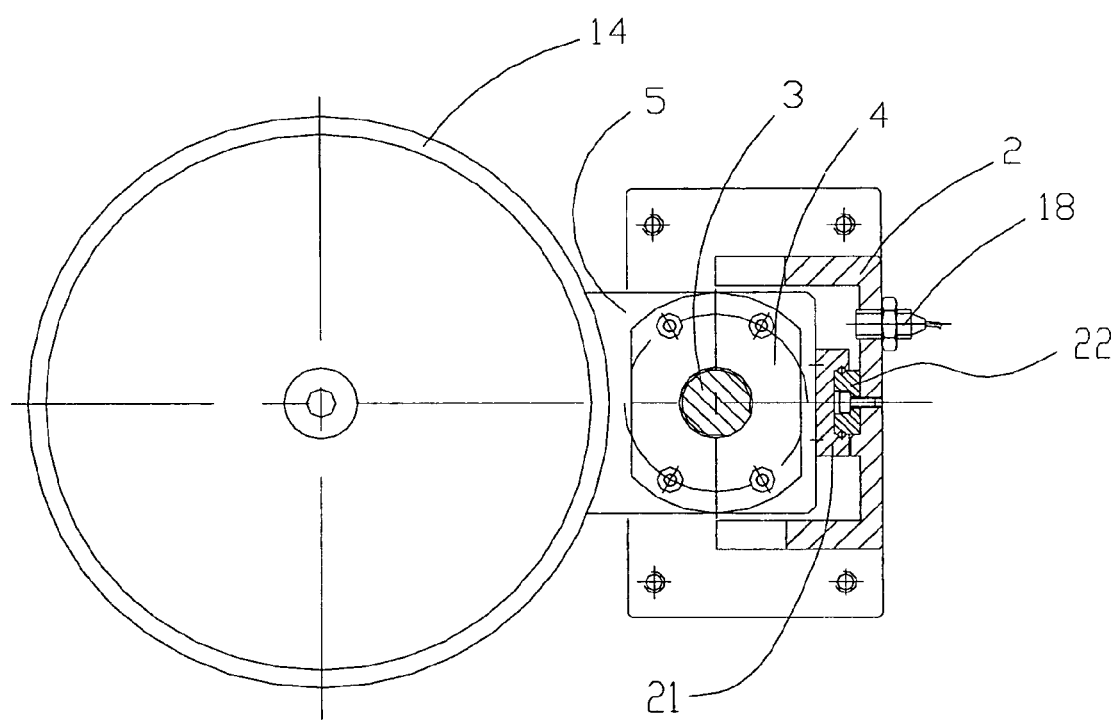
FIG. 4 is a sectional view of FIG. 3 along line B-B.

FIGS. 3 and 4 show another embodiment of the present invention. Compared with that illustrated in FIGS. 1 and 2, the V-shape grooves 19 on the two side walls of the linear slide rail 2 and the V-shape bosses 20 on the two side walls of the slider bracket 5 are replaced with a ball type linear slide bearing 22 provided on the linear slide rail 2 and an embedding block 21 provided at the outer edge of the slider bracket 5. The embedding block 21 can be connected with the ball type linear slide bearing 22. Thus, the outer edge portion of the bracket can be movably embedded with the linear slide bearing for linear constraint.

The present invention, in use, is controlled by each electric control systems, and the lifting of the slider bracket 5 together with the turntable is controlled by the first motor 10 via the rotation of the lead screw 3 while the second motor 12 directly controls the rotation of the turntable 14. Each proximity switch 18 controls the lifting positions of the lifting apparatus.

The lifting apparatus provided by the present invention can be applied in a safety inspection system, such as a CT detection device 23 provided above the turntable device, which generally comprises an X-ray generator, a detector, a scanner, an imaging device and a control device thereof which are conventional art. Therefore, further detailed description thereof is omitted herein.

Although a preferred embodiment has been illustrated and described, it would be appreciated by those persons skilled in the art that the present invention may be made in any other mode without departing from the principles and spirit of the invention as defined by the appended claims of this invention and their equivalent thereof.

The invention claimed is:

1. A lifting apparatus, comprising:
a vertical guide device;
a turntable device which is movable along the vertical guide device upwards or downwards; and
a first driving device which drives the turntable device moving upwards or downwards guided by the vertical guide device,
wherein said turntable device comprises:
a bracket which is slidably engaged with the vertical guide device and projects perpendicularly toward a side of the vertical guide device;
a turntable which is rotatably provided on an upper part of the bracket;
a second driving device which is provided on a bottom surface of the bracket to rotate the turntable on the bracket; and
a first radial bearing for positioning the turntable and a first thrust bearing for bearing a load of the turntable on the bracket in the vertical direction, the first radial bearing and first thrust bearing being located between the turntable and the bracket,
wherein said vertical guide device comprises:
a linear slide rail, an outer edge of the bracket is movably embedded with the linear slide rail to form linear constraint therebetween in a manner such that V-shape bosses are provided on the bracket and V-shape grooves mated with the V-shape bosses are provided on the linear slide rail;
a lead screw which is provided in the linear slide rail, with the first driving device provided at an end of the linear slide rail to drive the lead screw to rotate; and
a nut which is fixed on the bracket and engaged with the lead screw.

2. The lifting apparatus according to claim 1, wherein, an upper bearing seat and a lower bearing seat are provided at a respective end of the linear slide rail, the lead screw being engaged with the upper bearing seat and lower bearing seat.

3. The lifting apparatus according to claim 2, wherein, the lower bearing seat comprises a second radial bearing for positioning the lead screw and a second thrust bearing for bearing a load applied on the lead screw in the vertical direction.

4. The lifting apparatus according to claim 1, wherein, an outer edge of the bracket is movably embedded with the linear slide rail in a manner that a ball type linear slide bearing is provided on the linear slide rail and the outer edge of the slider bracket is provided with an embedding block connected with the ball type linear slide bearing.

5. The lifting apparatus according to claim 1, wherein, proximity switches for limiting position and protecting function are provided at the top and bottom of the linear slide rail.

6. The lifting apparatus according to claim 1, wherein, a flexible coupling is provided between an end of the lead screw and the first driving device.

7. The lifting apparatus according to claim 1, wherein, a counter bore for centrally positioning a standard sample is provided at a central place of the turntable, and a rubber pad is provided on the turntable.

8. The lifting apparatus according to claim 1, wherein, a power transmission opening of the second driving device is provided with a cable chain projecting from the guide device.

9. A safety inspection system, comprising:
a lifting apparatus according to claim 1; and
a CT detection device provided over the turntable device.

* * * * *